US009055985B2

(12) United States Patent
Lazarof

(10) Patent No.: US 9,055,985 B2
(45) Date of Patent: Jun. 16, 2015

(54) DENTAL ABUTMENT WITH COVER

(76) Inventor: Sargon Lazarof, Woodland Hills, CA (US)

( * ) Notice: Subject to any disclaimer, the term of this patent is extended or adjusted under 35 U.S.C. 154(b) by 357 days.

(21) Appl. No.: 13/298,744

(22) Filed: Nov. 17, 2011

(65) Prior Publication Data

US 2012/0064488 A1    Mar. 15, 2012

Related U.S. Application Data

(63) Continuation-in-part of application No. 12/012,278, filed on Feb. 1, 2008, now Pat. No. 8,828,066.

(60) Provisional application No. 60/899,245, filed on Feb. 1, 2007.

(51) Int. Cl.
*A61C 8/00* (2006.01)
*A61B 17/86* (2006.01)

(52) U.S. Cl.
CPC ......... *A61B 17/8625* (2013.01); *A61B 17/8685* (2013.01); *A61B 2017/8655* (2013.01); *A61C 8/00* (2013.01); *A61C 8/0022* (2013.01); *A61C 8/0033* (2013.01); *A61C 8/006* (2013.01); *A61C 8/0068* (2013.01); *A61C 8/0071* (2013.01)

(58) Field of Classification Search
CPC .... A61C 8/0071; A61C 8/0033; A61C 8/006; A61C 8/0068; A61C 8/0022
USPC .................................................. 433/172–176
See application file for complete search history.

(56) References Cited

U.S. PATENT DOCUMENTS

| | | |
|---|---|---|
| 3,708,883 A | 1/1973 | Flander |
| 5,004,421 A | 4/1991 | Lazarof |
| 5,087,199 A | 2/1992 | Lazarof |
| 5,762,500 A | 6/1998 | Lazarof |
| 5,882,200 A | 3/1999 | Sutter et al. |
| 5,989,026 A * | 11/1999 | Rogers et al. ................. 433/172 |
| 6,048,203 A | 4/2000 | Rosenberg |
| 6,142,782 A | 11/2000 | Lazarof |
| 6,419,492 B1 | 7/2002 | Schroering |

(Continued)

FOREIGN PATENT DOCUMENTS

EP     0957811 B1     10/2004

OTHER PUBLICATIONS

"Thinking of Switching from 3i Implants to Ankylos: Any thoughts?" Posted in Active Posts Advice Dental Implant Systems Surgical Placement of Dental Implants, 1 page.

(Continued)

*Primary Examiner* — Ralph Lewis
(74) *Attorney, Agent, or Firm* — Caesar Rivise, PC

(57) ABSTRACT

A dental implant assembly comprises an implant body adapted for securement within a bore in a jaw bone of a patient. The implant body has a portion with an external thread for engaging the bore. An abutment has a top portion and a bottom portion. The top portion of the abutment is adapted to secure a prosthetic component. The bottom portion of the abutment is attachable to the implant body and adapted to be positioned below a gumline of the patient, the abutment formed of a first material. A cover is sized and shaped to cover the bottom portion of the abutment and adapted to be positioned below the gum line, without covering the top portion of the abutment. The cover is formed from a second material having a different color from the first material.

16 Claims, 13 Drawing Sheets

(56) References Cited

U.S. PATENT DOCUMENTS

| | | | |
|---|---|---|---|
| 6,726,481 B1 * | 4/2004 | Zickmann et al. | 433/173 |
| 7,677,891 B2 | 3/2010 | Niznick | |
| 8,128,670 B2 | 3/2012 | Ralph et al. | |
| 2004/0234925 A1 * | 11/2004 | Benhamou | 433/173 |
| 2005/0084819 A1 * | 4/2005 | Sims et al. | 433/173 |
| 2006/0121417 A1 * | 6/2006 | Scommegna et al. | 433/173 |
| 2008/0208264 A1 | 8/2008 | Lazarof | |
| 2009/0123888 A1 | 5/2009 | Rosenberg | |
| 2009/0123891 A1 | 5/2009 | Rosenberg | |

OTHER PUBLICATIONS

"Morse Taper to Reduce Microbial Leakage," Osteo-Ti, 2011, 1 page.

* cited by examiner

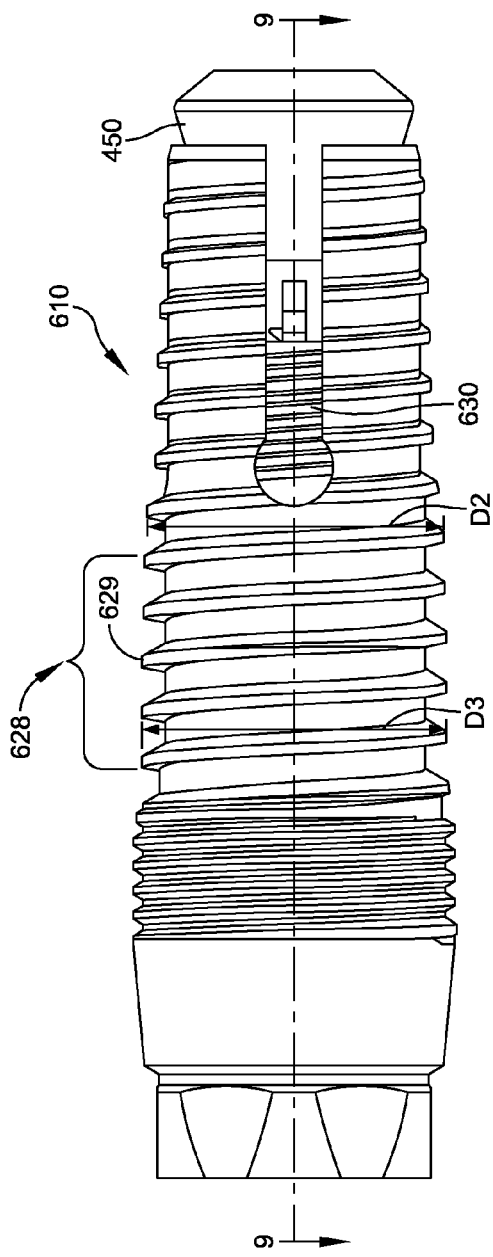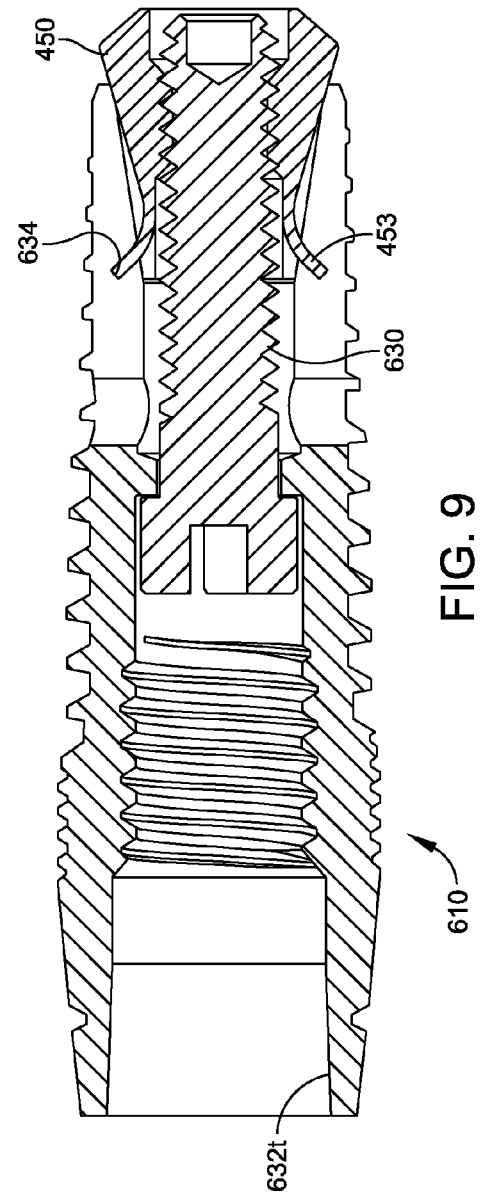
FIG. 8
FIG. 9

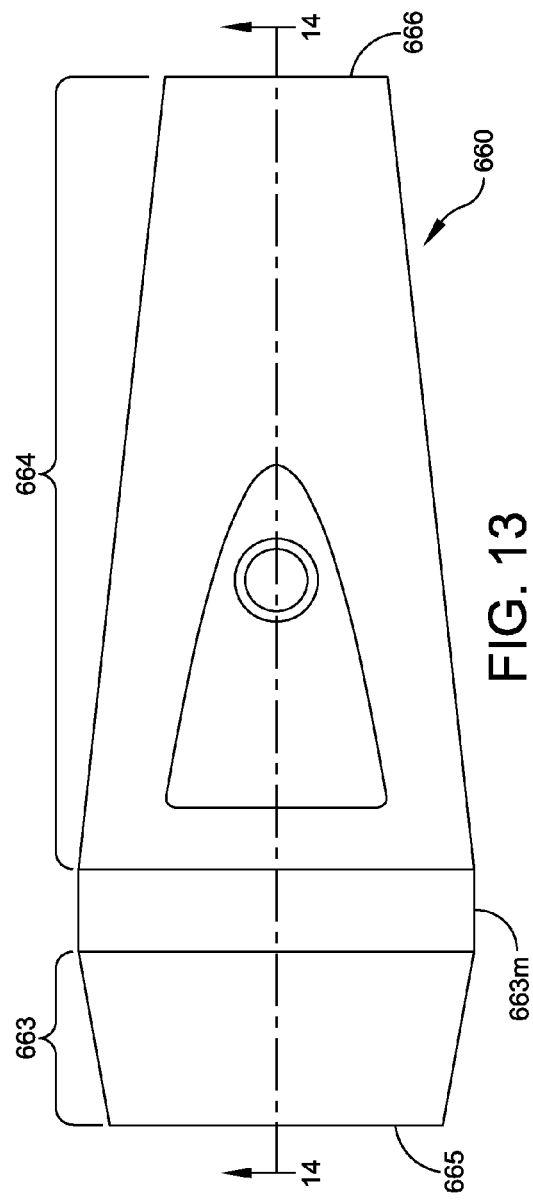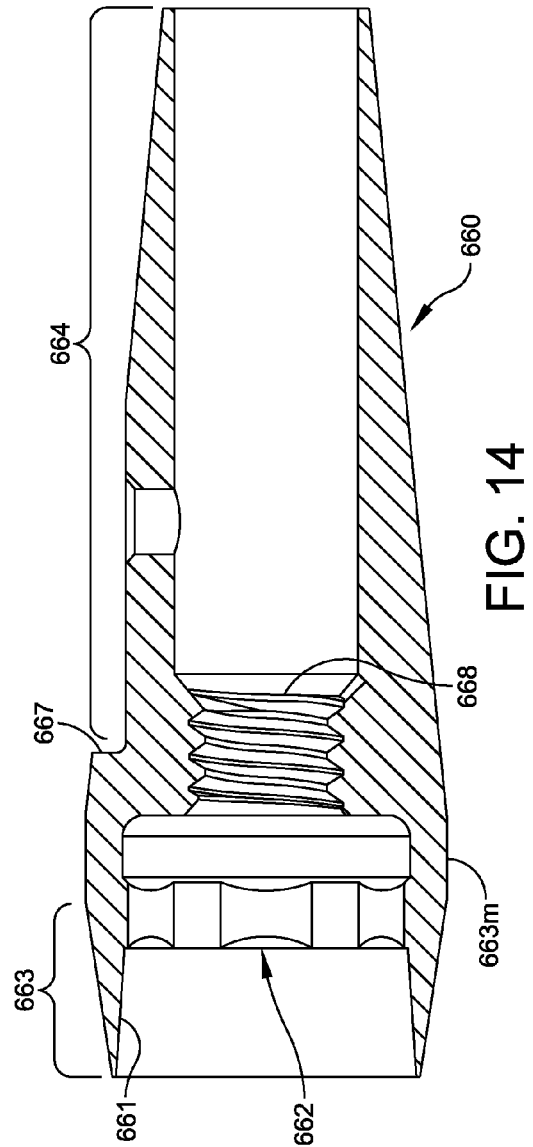

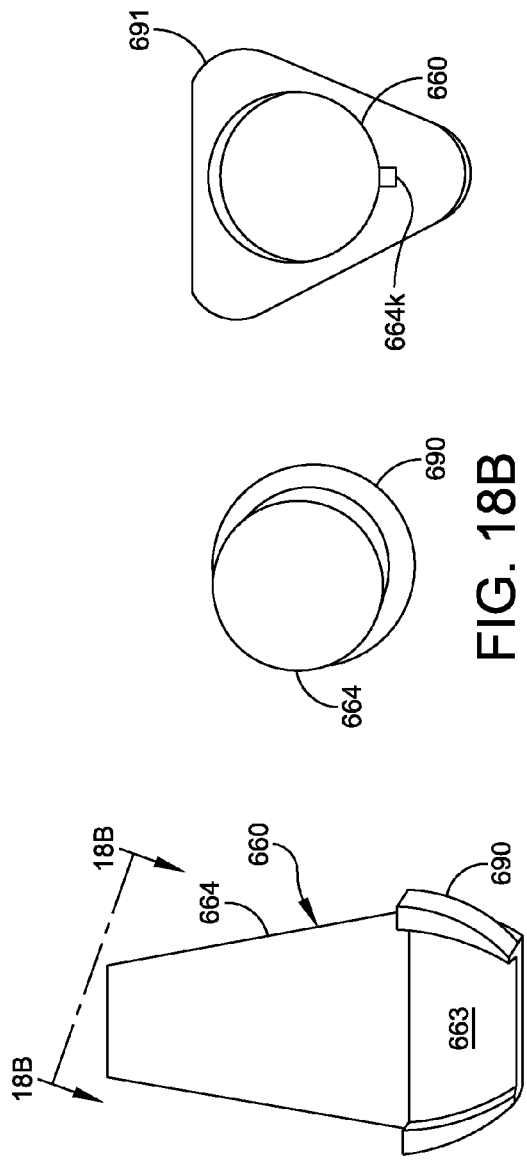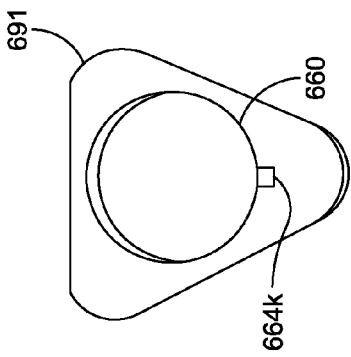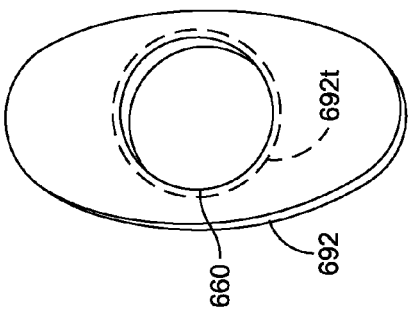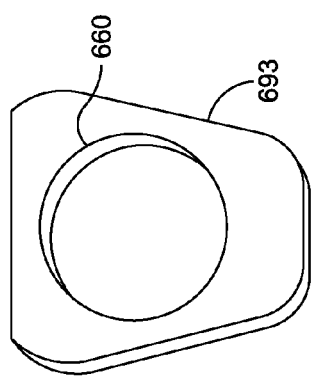

DENTAL ABUTMENT WITH COVER

This application is a continuation-in-part of U.S. patent application Ser. No. 12/012,278, filed Feb. 1, 2008, and claims priority to U.S. Provisional Patent Application No. 60/899,245 filed on Feb. 1, 2007, both of which are expressly incorporated by reference herein in their entireties.

FIELD

This disclosure relates to dental implants and securing mechanisms for the implants.

BACKGROUND

Medical/dental devices are provided for fixing bone fractures, anchoring of bones, or anchoring of prosthetics to bones. The device generally relates to molly bolts, expandable screws, or devices/screws with expansion or locking mechanisms. In some embodiments, an implant assembly includes a tubular body portion that can be positively secured within a bore in a bone or prosthetic by expander mechanism at both ends of the tubular body portion.

Use of mechanical locking means for securing bone fractures, anchoring of bones, or anchoring of prosthetic to bone are old in the art. Exemplary of such devices is the device described in U.S. Pat. No. 3,708,883 issued to Flander. An improved dental implant is illustrated and described in U.S. Pat. Nos. 5,004,421 and 5,087,199 issued to Lazarof. The Lazarof dental implant makes use of mechanical securement means. In one form, the Lazarof implant is positively secured within the bore in the bone by two separate but cooperating securement mechanisms. The first securement mechanism comprises self-tapping, external threads provided on the tubular body of the device which are threaded into the bone by rotating the device in a first direction. The second cooperating securement mechanism comprises a plurality of bone penetrating anchor blades formed on the skirt portion of the tubular body which are moved into a bone engagement position only after the implant has been secured into the bone. The anchor blades are moved into the bone engagement configuration by rotating a threaded expander member also in a first direction.

SUMMARY

In some embodiments, a dental implant assembly comprises an elongated tubular body adapted for securement within a bore in a jaw bone of a patient. The body has an expandable bottom portion. The expandable bottom portion has an outer thread on an outer surface thereof. The outer thread has a major diameter that gradually increases from a first major diameter near a bottom end of the body to a second major diameter near a top end of the bottom portion. The top end of the bottom portion is located between the bottom end of the body and the top end of the body. An expander at least partially extends into the bottom end of the tubular body. The expander is configured to be advanced from a first position in which the bottom portion of the body is not expanded to a second position in which the expander forces the bottom portion of the body to expand in diameter.

In some embodiments, a dental implant assembly comprises an implant body adapted for securement within a bore in a jaw bone of a patient. The implant body has a portion with an external thread for engaging the bore. An abutment has a top portion and a bottom portion. The top portion of the abutment is adapted to secure a prosthetic component. The bottom portion of the abutment is attachable to the implant body and adapted to be positioned below a gumline of the patient, the abutment formed of a first material. A cover, is sized and shaped to cover the bottom portion of the abutment and adapted to be positioned below the gum line, without covering the top portion of the abutment. The cover is formed from a second material having a different color from the first material.

In some embodiments, a dental implant assembly comprises an implant body having a bottom portion adapted for securement within a bore in a jaw bone of a patient. The implant body has a top portion with an external tapered surface. An abutment has a top portion adapted to secure a prosthetic component and a bottom portion adapted to be positioned below a gumline of the patient. The bottom portion of the abutment is shaped to attach to and fit over the implant body. The bottom portion of the abutment has a cavity with an internal tapered surface. The internal tapered surface of the abutment and the external tapered surface of the implant body form a Morse taper.

In some embodiments, an assembly comprises an abutment having a top portion and a bottom portion, the top portion of the abutment adapted to secure a prosthetic component, the bottom portion of the abutment attachable to an implant body within a bore in a jaw bone of a patient, the abutment formed of a first material. A cover is sized and shaped to cover the bottom portion of the abutment without covering the top portion of the abutment, The cover is formed from a second material different from the first material.

In some embodiments, a dental implant assembly comprises an elongated tubular body adapted for securement within a bore in a jaw bone of a patient, the body having an expandable bottom portion, the body having a first top portion with an internal taper. An expander, at least partially extends into the bottom end of the tubular body. The expander is configured to be advanced from a first position in which the bottom portion of the body is not expanded and a second position in which the expander forces the bottom portion of the body to expand in diameter. A first screw is provided in the top end of the body. The first screw has a tapered head capable of forming a Morse taper seal with the internal taper of the first top portion.

In some embodiments, a method comprises providing an abutment having a top portion and a bottom portion, the top portion of the abutment adapted to secure a prosthetic component, the abutment formed of a first material; covering the bottom portion of the abutment with a cover, without covering the top portion of the abutment, the cover formed from a second material having a different color from the first material; and securing the bottom portion of the abutment to an implant body implanted within a bore in a jaw bone of a patient.

In some embodiments, a method comprises attaching an abutment to an implant body so as to form a seal therebetween and cover the implant body, the implant body having a top portion with an external tapered surface and a bottom portion secured within a jaw bone of a patient, the abutment having a top portion adapted to secure a prosthetic component and a bottom portion adapted to be positioned below a gumline of the patient. The bottom portion of the abutment is shaped to attach to and fit over the implant body. The bottom portion of the abutment has a cavity with an internal tapered surface. The internal tapered surface of the abutment and the external tapered surface of the implant body form a Morse taper.

BRIEF DESCRIPTION OF THE DRAWINGS

FIG. 8 is a side view of the implant of FIG. 7.

FIG. 9 is a cross-sectional view of the implant of FIG. 8, taken along section line 9-9.

FIG. 13 is a side view of the abutment shown in FIG. 6.

FIG. 14 is a cross sectional view of the abutment taken along section line 14-14 of FIG. 13.

FIGS. 18A and 18B are partial cutaway and top views of the cover of FIG. 17.

FIGS. 18C to 18E show variations of the abutment/cover sub-assembly of FIG. 18A.

DETAILED DESCRIPTION

Figure 1:
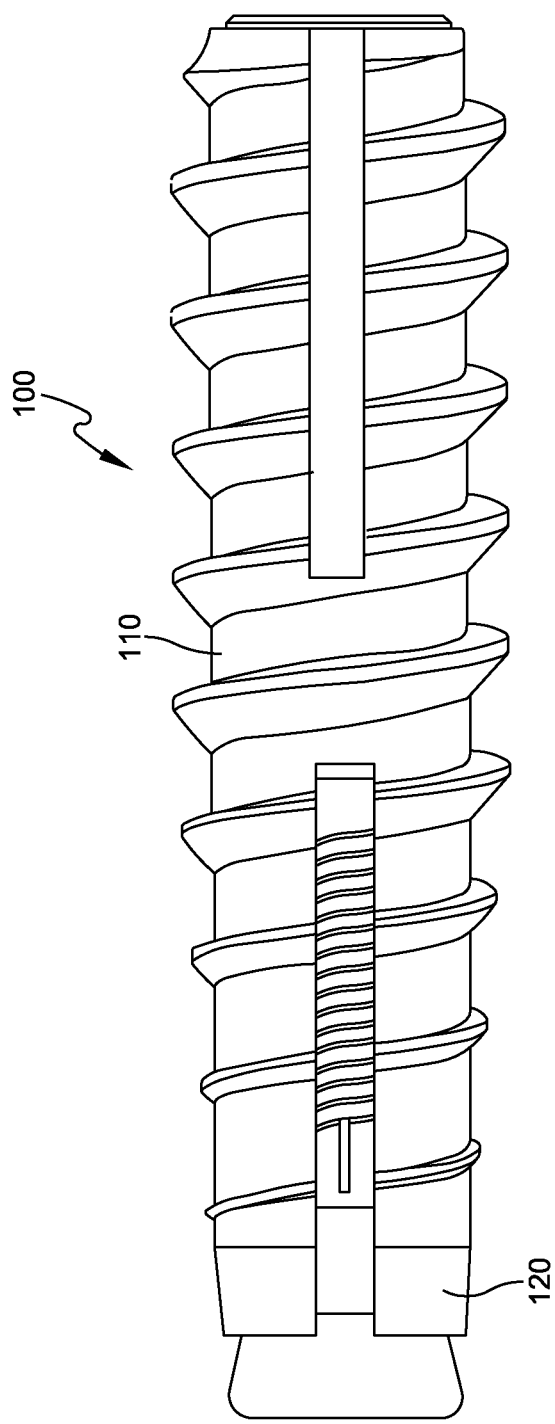
FIGS. 1 through 3 shows an embodiment of the device.
Figure 2:
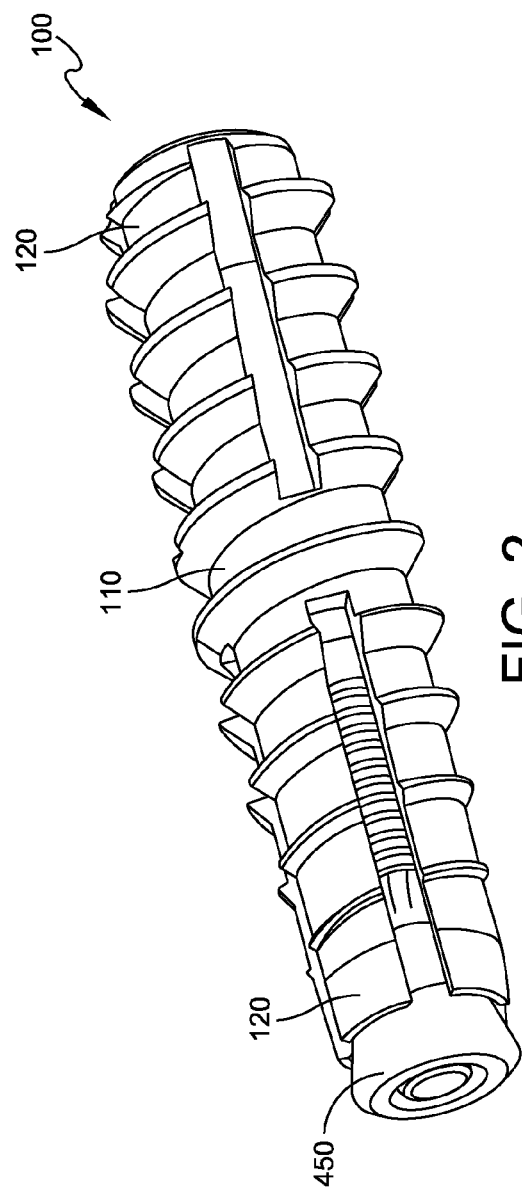
Figure 3:
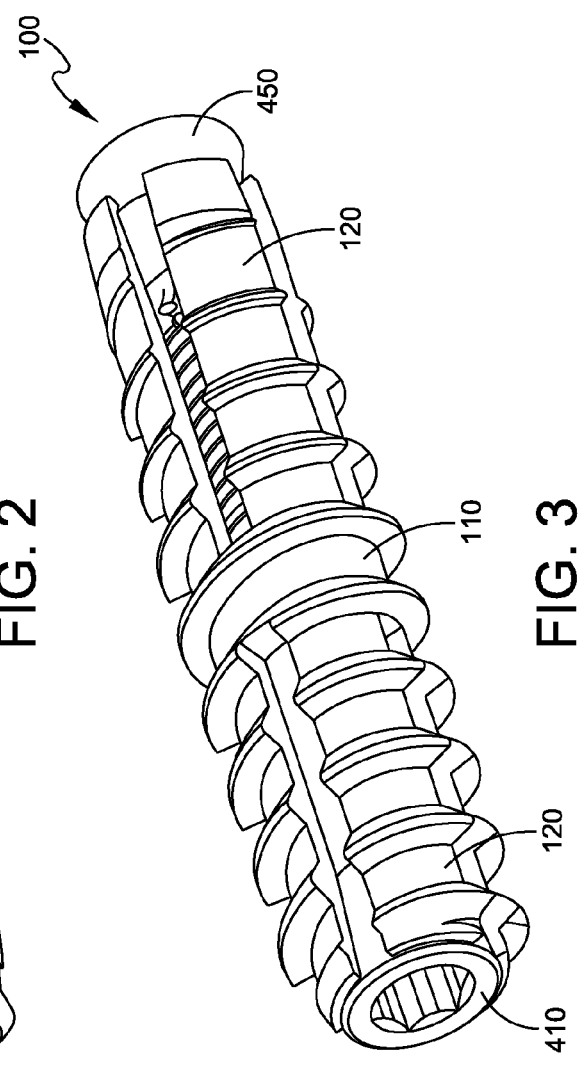
Figure 4:
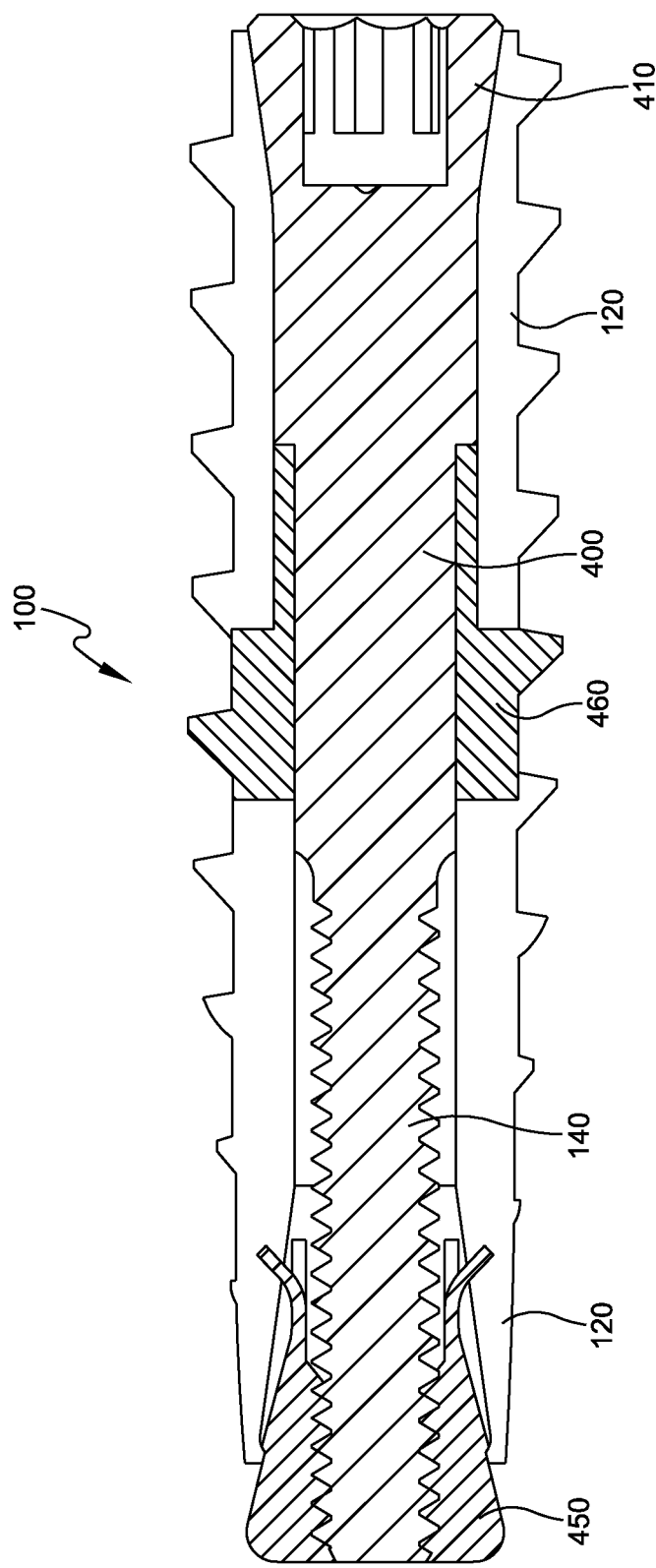
FIGS. 4 and 5 are cut out views of an embodiment of the device.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

REFERENCE NUMBERS

100 . . . Securing Device [0010] 110 . . . Hollow Body [0011] 120 . . . Skirt [0012] 400 . . . Draw Screw [0013] 410 . . . Draw Screw Head [0014] 440 . . . Threaded Shank [0015] 450 . . . Expansion Nut [0016] 460 . . . Blocking Edge In some embodiments, a device is provided for securing two components together, namely, prosthetics-to-bone, or bone-to-bone, etc. The device comprises an elongated hollow body with expandable skirts at both ends of the elongated hollow body. The device further comprises a draw screw having a head captured within the hollow body that engages the internal of the hollow body. The device further comprises a threaded shank at the end of the draw screw head which extends to an end of one skirt. At the end of the threaded shank is an expansion nut for expanding the skirt at this end of the device.

FIGS. 1 through 4 disclose an example of the device 100. The device 100 comprises an elongated hollow body 110 with expandable skirts 120 at both ends of the elongated hollow body 110. The device 100 further comprises a draw screw 400 having a head 410 captured within the hollow body 110 that engages the internal of the hollow body 110. The device 100 further comprises a threaded shank 440 at the end of the draw screw head 410 which extends to an end of one skirt 120.

At the end of the shank 440 of the draw screw 400 is an expansion nut 450 having a skirt-engaging side wall and an inner threaded cavity. Rotation of the draw screw 400 through the inner cavity of the expansion nut 450 causes radial movement of the skirts 120 from the first retracted position to the second expanded position. The expansion nut 450 may be eliminated if expansion of the skirts 120 at the end farthest away from the head 410 is not desired.

The head 410 of the draw screw 400 is flared, whereby rotation of the draw screw 400 through the inner cavity of the hollow body chamber 220 causes radial movement of the skirt 120 from the first retracted position to the second expanded position. The interior of the elongated hollow body 110 further comprises a blocking edge 460 for stopping the movement of the expansion nut 450. While the head 410 of the draw screw 400 may be flared, in an alternative form, the head can be unflared such that rotation of the draw screw 400 in the expansion direction will not cause the skirt 120 closes to the head 410 to expand.

To further aid in the expansion, skirt 120 may include an inclined internal surface. The skirt-engaging side wall of the expansion nut 450 may also have an inclined external surface moveable into engagement with the inclined internal surface of the skirt 120 upon rotation of the draw screw 400 through the inner cavity of the expansion nut 450. The skirt 120 may also be split such that at least two anchor segments movable from the first retracted position to the second expanded position is created. The split in the skirt may be a plurality of circumferentially spaced, longitudinally extending slits which separate the anchor segments.

The exterior of the elongated hollow body chamber 220 may be threaded such that selected components may be threadably connected. The threading prevents the device 100 from sliding out of the connection points created in the components to be connected.

To use the device 100 two holes are created, one in each of the two components to be connected. The holes should be the same size or slightly larger than the outer diameter of the device 100. Ideally, the end with the expansion nut 450 would be placed into the first hole. The draw screw 400 is rotated such that the expansion nut 450 travels up the threaded shank 440. As the expansion nut 450 travels up the threaded shank 440, the skirt 120 is pushed out and expands to secure to the first component.

The second component to be attached to the first component is then inserted such that the protruding end of the device 100 passes into the hole in the second component. The hole in the second component may be drilled through so that the draw screw head 410 is accessible. Since the expansion nut 450 is blocked from further movement by the blocking edge 460, continued rotation of the draw screw 400 causes the draw screw 400 to move towards the center of the device 100. As the draw screw 400 moves towards the center of the device 100, the flanged head on the draw screw 400 causes the skirt 120 closes to the draw screw head 410 end to expand. The expansion of the skirt 120 secures the device 100 to the second component which in turns connects the first component to the second component.

Alternatively, instead of having a hole that provides access to the draw screw head 410, the draw screw head 410 may be magnetic. A head 410 with magnetic characteristics allows the draw screw 400 to be rotated with a magnetized screw or drill. As the draw screw is rotated, the skirt 120 expands to secure the device 100 to the second component which in turns connects the first component to the second component.

Figure 5:
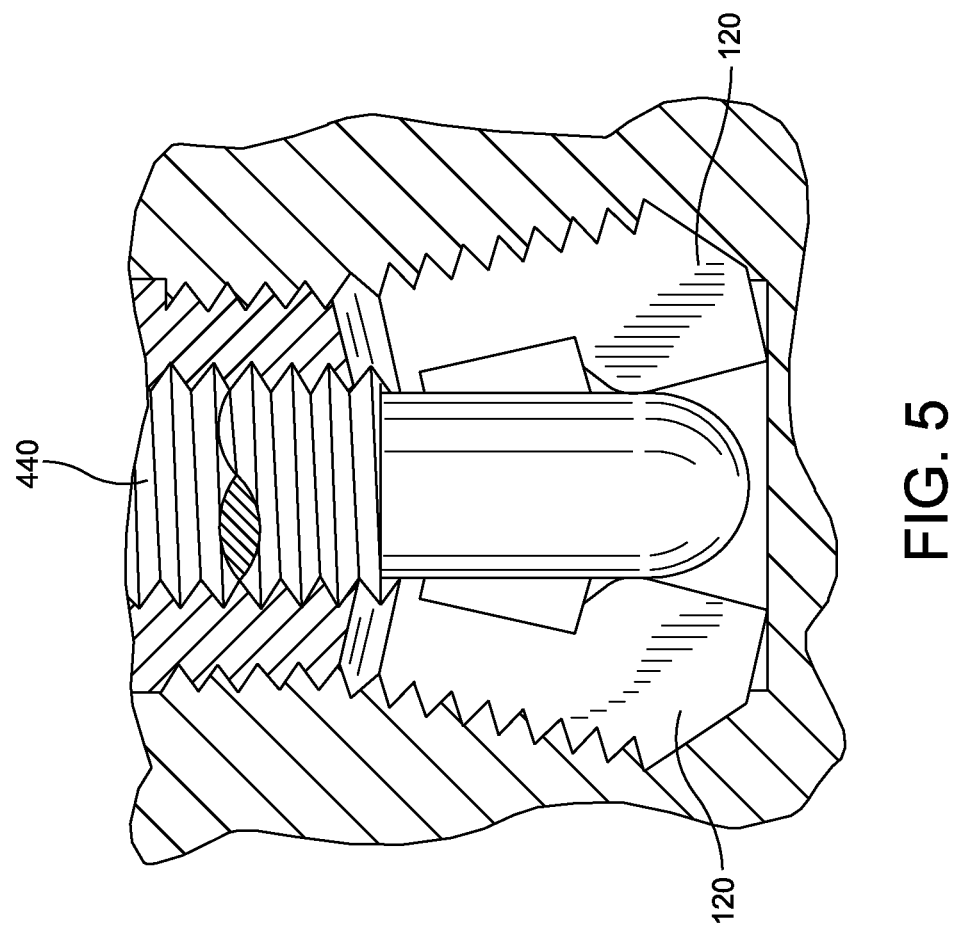

In an alternative embodiment of the device 100 as shown in FIG. 5, the interior of the skirts 120 farthest away from the draw screw head 410 is enlarged such that the passageway from the hollow body 110 through the skirts 120 are narrowed or closed completely. The initial starting position of the threaded shank 440 would be within the hollow body 110 and may be just beyond the enlarged section of the skirts 120. All other aspects of the device 100 may be similar to those discussed above.

In another embodiment of the device 100 in this alternative form, the flare on the head 410 may be eliminated such that the skirts 120 closest to the head 410 is not expanded.

In another embodiment of the device 100 in this alternative form, the enlargement of the interior of the skirts 120 is removed such that the skirts 120 at the end farthest from the head is not expanded when the draw screw 400 is rotated into the expanded position.

To use the device 100 in this alternative form, the device 100 is inserted into prepared holes in objects to be connected. As the draw screw 400 is rotated in the proper direction for expansion, both the skirts 120 farthest away from the draw screw head 410 and the skirts 120 closest to the draw screw head 410 are forced to expand due to the pushing of the farthest skirts 120 by the threaded shank 440 and the draw screw head 410 on the closest skirts 120, respectively. The expansion of both skirts 120 causes a tight connection between the components to be joined.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Figure 6:
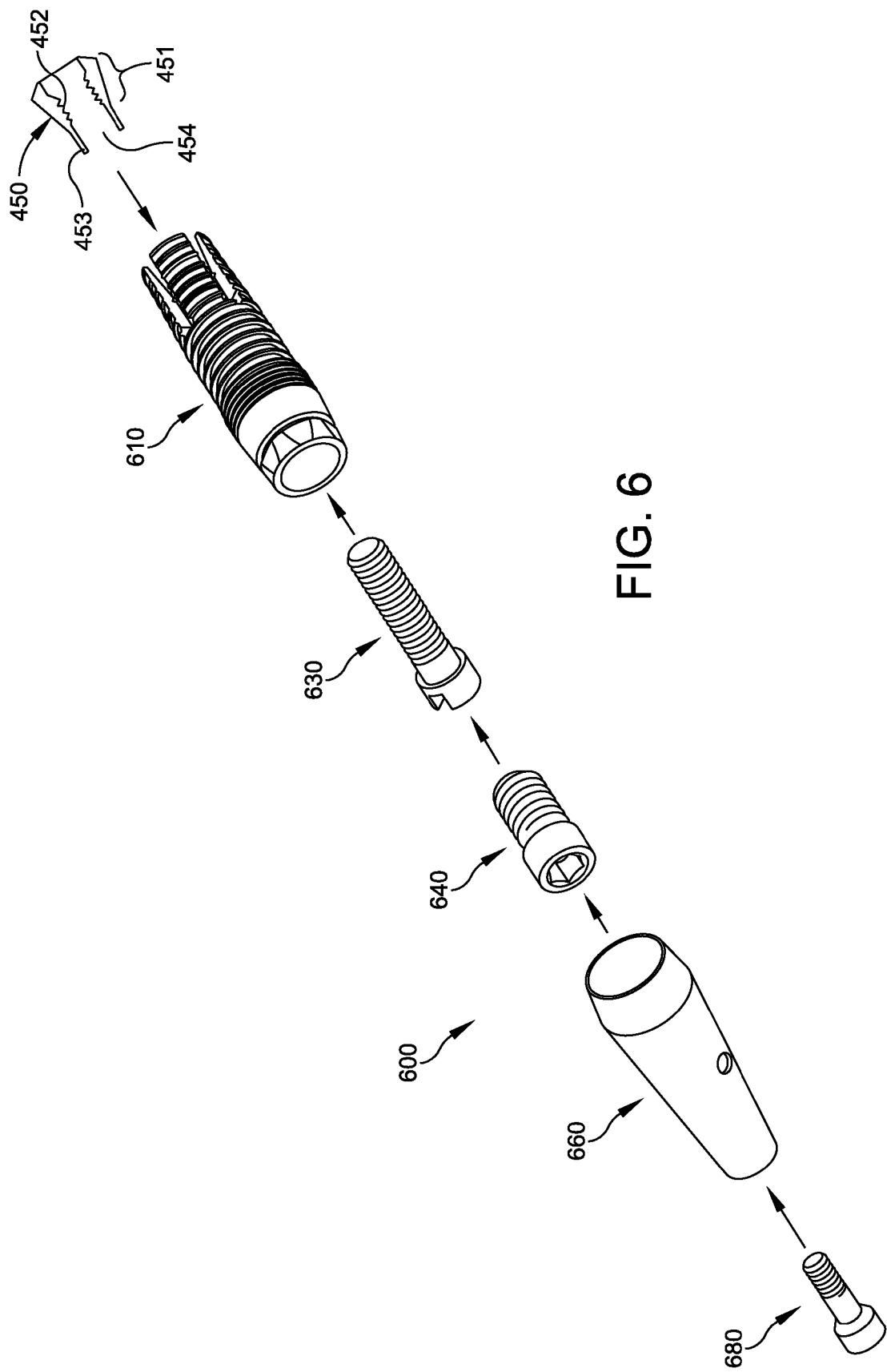
FIG. 6 is an exploded view of the implant and abutment.
Figure 7:
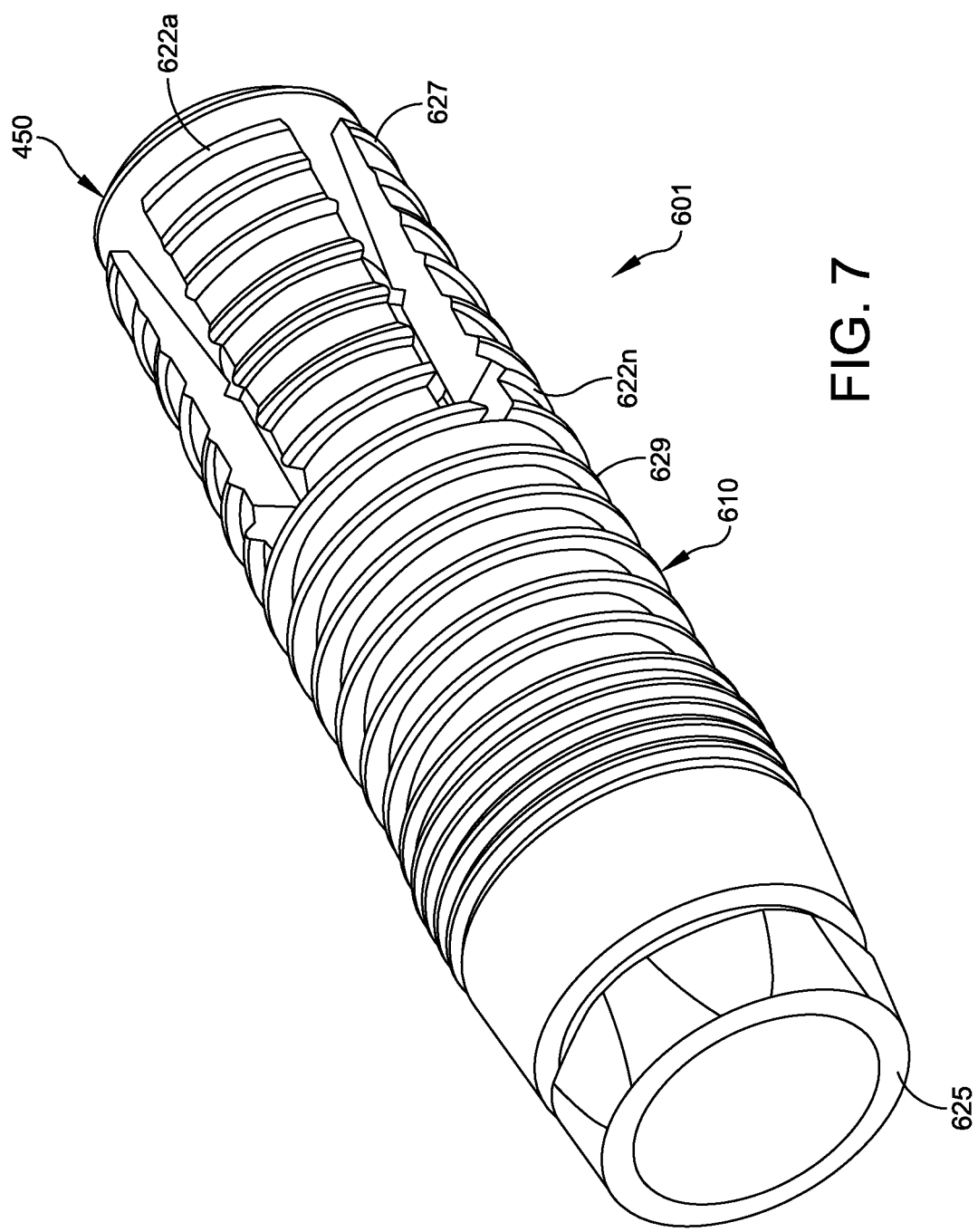
FIG. 7 is an isometric view of the implant, without the abutment.
Figure 12:
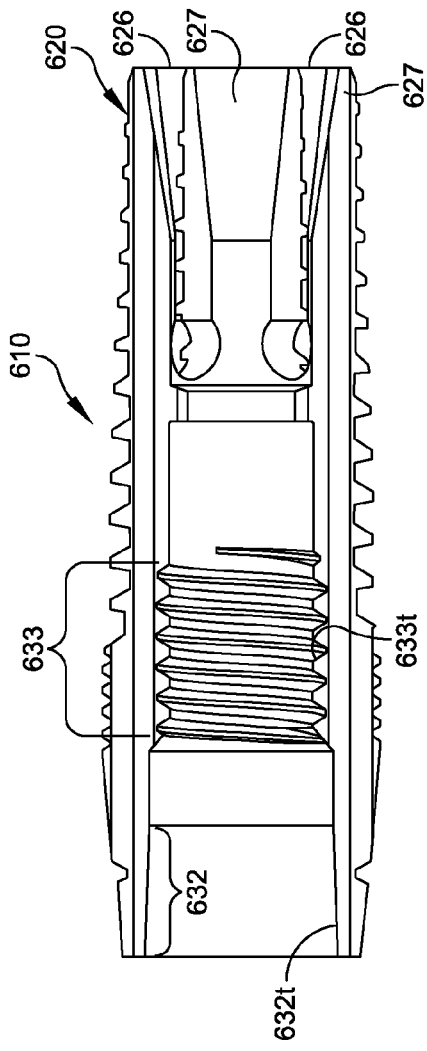
FIG. 12 is a cross-sectional view of the implant body of FIG. 11, taken along section line 12-12.
Figure 10:
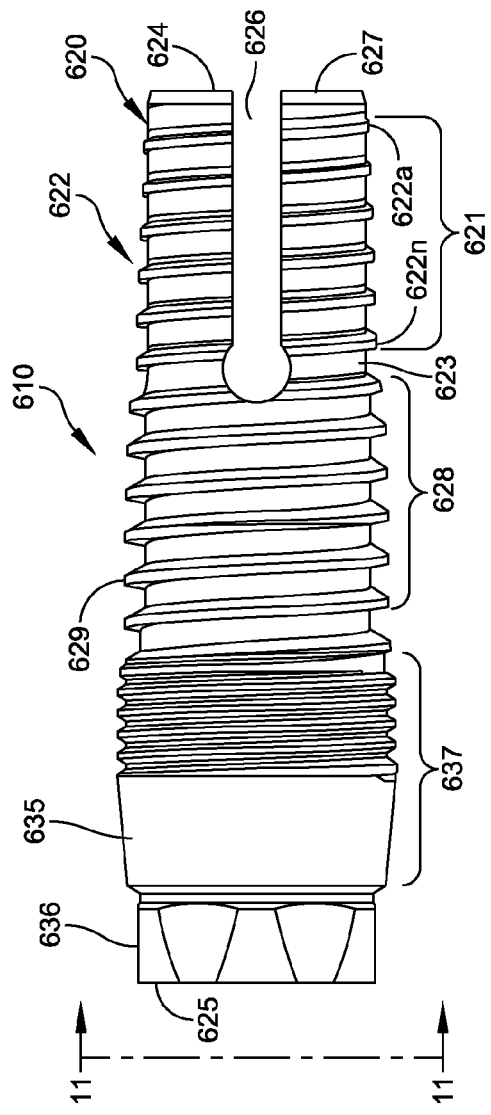
FIG. 10 is a side view of the implant body of FIG. 6.
Figure 11:
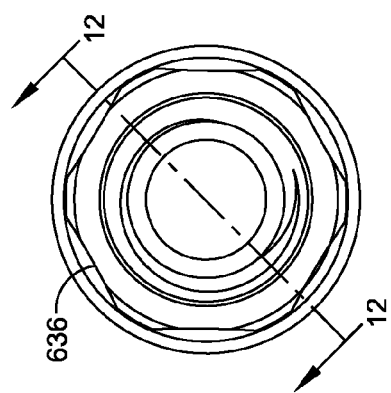
FIG. 11 is an end view of the implant body as viewed from section line 11-11 of FIG. 10.

FIGS. 6-12 show another embodiment of a dental implant assembly 600. FIG. 6 is an exploded view of the implant 601 and abutment 660. FIG. 7 is an isometric view of the implant 601, without the abutment 660. FIG. 8 is a side view of the implant 601 of FIG. 7. FIG. 9 is a cross-sectional view of the implant 601 of FIG. 8, taken along section line 9-9. FIG. 10 is a side view of the implant body 610 of FIG. 6. FIG. 11 is an end view of the implant body 610 as viewed from section line 11-11 of FIG. 10. FIG. 12 is a cross-sectional view of the implant body 610 of FIG. 11, taken along section line 12-12.

As best seen in FIGS. 10-12, implant assembly 600 has an elongated tubular body 610 adapted for securement within a bore 740 (FIG. 19) in a jaw bone 750 (FIG. 19) of a patient. Referring again to FIGS. 6-12, the body 610 has an expandable bottom portion 621. The expandable bottom portion 621 has an outer thread 622 on an outer surface thereof. The outer thread 622 has a major diameter that gradually increases from a first major diameter 622a near a bottom end 624 of the body 610 to a second major diameter 622n near a top end 623 of the bottom portion 621. The top end 623 of the bottom portion 621 is located between the bottom end 624 of the body 610 and the top end 625 of the body. The difference between the major diameter and minor diameter of threads 622 also gradually increases from the bottom end 624 to the top end 623 of the bottom portion 621.

The expandable bottom portion 621 includes a plurality of longitudinal slots 626 separating the expandable portion into anchoring segments 627. The body 610 also includes a middle portion 628 between the top end 623 of the bottom portion 621 and the top end 625 of the body. The middle portion 628 has an outer thread 629 with a major diameter that increases from the second major diameter D2 (FIG. 8) to a third major diameter D3 (FIG. 8). The height of the threads 629 (i.e., the difference between the major and minor diameters of the threads) may be constant throughout the middle portion, but there may be a small change increase in the major diameter towards the top of the middle portion, to facilitate self tapping. Throughout the middle portion 628 the outer thread 629 has a major diameter that is greater than the second major diameter 622n. The major diameter 629 of the middle portion is sized and shaped to engage the bore 740 of the jaw and tap an internal thread in the bore 740.

Even the largest thread 622n of the bottom portion 621 is substantially smaller in major diameter than the threads 629 of the middle portion. During tapping and insertion of the implant assembly, the threads 622a-622n of the bottom portion 621 do not engage the wall of the bore 740. Because the anchoring segments 627 of the bottom portion 621 are cantilevered, they are subject to bending much more than the middle section 628. By sizing the threads 622a-622n smaller than the tapping threads 629 of the middle section, the anchoring segments 627 are protected from damage during the tapping of the bore 740 by the threads 629.

An expander 450 at least partially extends into the bottom end 624 of the tubular body 610. The expander may be, for example, of the type shown and described above with reference to FIGS. 1-4. The expander 450 has a portion 451 that is frustum shaped. Other flared expanders configured to controllably advance into the bottom end of the tubular body 610 may be substituted. The expander 450 has an internal thread 452 engaged by a draw screw 630. The expander 450 is configured to be advanced by rotation of the draw screw 630 from a first position in which the bottom portion 621 of the body 610 is not expanded and a second position in which the expander 450 forces the bottom portion 621 of the body 610 to expand in diameter.

At least a portion 451 of the expander 450 has an outer diameter that decreases towards a top end 454 of the expander. The top end 454 of the expander extends into the body 610. The top end 454 has fingers 453. Slots 634 (FIG. 9) within the body 610 receive the fingers 453. When the fingers 453 reach the end of the slots, further advancement of the expander 450 into the body 610 is limited. This provides a positive feel to the doctor when the fingers 453 engage the slots 634, and helps prevent overtightening.

The rotatable draw screw 630 is at least partially contained within the implant body 610 and at least partially contained within the top end 454 of the expander 450. The draw screw 630 has a threaded portion 631 engaging the internal thread 452 of the expander 450, so that rotation of the draw screw 630 causes the expander 450 to advance towards the top end 625 of the body 610.

Thus, in embodiments having threads in the middle portion 628 with a major diameter substantially greater than the major diameter of the largest thread in the expandable bottom portion 621, the doctor is provided greater flexibility for installation. For example, the doctor can insert the implant assembly 601 like a regular self-tapping screw without pre-tapping the bore 740, where the bore 740 is sized for a screw type implant having the major diameter of threads 629. If installed this way, the threads 629 of the middle portion 628 perform the self-tapping, without damaging the threads 622a-

622n. Threads 622a-622n do not engage the bore 740 during the tapping. Subsequently, when the expander 450 is advanced into the body 610, the anchoring segments 627 are pushed outward in the radial direction, forcing the threads 622a-622n of the bottom portion 621 to grip the interior walls of the bore 740. Thus, the threads 622a-622n are sized as not to engage the wall of the bore 740 when bottom portion 621 is not expanded and the threads 629 are tapping the bore 740; but the threads 622a-622n engage the wall at the bottom of the bore 740 for gripping when bottom portion 621 is expanded. Alternatively, the doctor can pre-tap the inside of the bore 740, insert the implant assembly 601, and expand the bottom portion 621.

A method of using the dental implant assembly 600 is provided, where the body 610 includes a middle portion 628 between the top end 623 of the bottom portion 621 and the top end 625 of the body 610, the middle portion 628 having an outer thread 629 with a major diameter that increases from the second major diameter D2 (FIG. 8) to a third major diameter D3 (FIG. 8). The threads 629 of the middle portion 628 are configured for tapping a thread in the bore 740 of the jaw. The method comprises forming the bore 740 in the jawbone 750 of the patient, so that the size of the bore 740 is greater than or equal to the second major diameter but less than the third major diameter; inserting the bottom portion 621 of the body into the bore 740 without interference between the thread 622 of the bottom portion 621 and a side wall of the bore 740; and tapping a thread in the bore 740 by engaging the middle portion 628 of the body with the side wall of the bore 740. The expander 450 is advanced towards the top end of the body 610 after the tapping step, so as to cause the expandable portion 621 of the body to expand outwardly and outer thread of the expandable portion to grip the side wall of the bore 740.

Although an example is provided in which the thread 629 and threads 622a-622n are combined with other features, such as particular tapers and abutments, this example is not limiting. The combination of thread 629 and threads 622a-622n may be used in any expandable dental implant assembly.

Referring now to FIGS. 10-14, another aspect is illustrated.

In the dental implant assembly of FIGS. 6-14, the body 610 has a first top portion 632 with an internal taper 632t and a second top portion 633 with an internal thread 633t. In FIG. 12, the second top portion 633 overlaps with the middle portion 628, but in other embodiments (not shown), the second top portion terminates closer to the top end 625, or the middle portion terminates closer to the bottom end 624, so that the second top portion does not overlap the middle portion.

A cover screw 640 is receivable in the top end 625 of the implant body 610. The cover screw 640 has a tapered head 641 with a tapered surface 641t capable of forming a seal with the internal taper 632t of the first top portion 632 of the body 610. In some embodiments, the tapered head 641 and the internal taper 632t form a Morse taper.

In typical use, implant 601 is expanded following insertion. The expander 450 has a tapered section 451 that forms a first seal with the bottom portion 621 of the implant body 610 when the draw screw 630 is rotated to advance the expander 450. However, in some instances, it is possible that the doctor may not advance the expander to the maximum extent possible, so that the first seal between the expander 450 and the bottom end 621 does not achieve its full sealing capability. For example, the doctor may use the expandable implant like a regular screw-type implant, without expanding the bottom portion 621.

Figure 15:
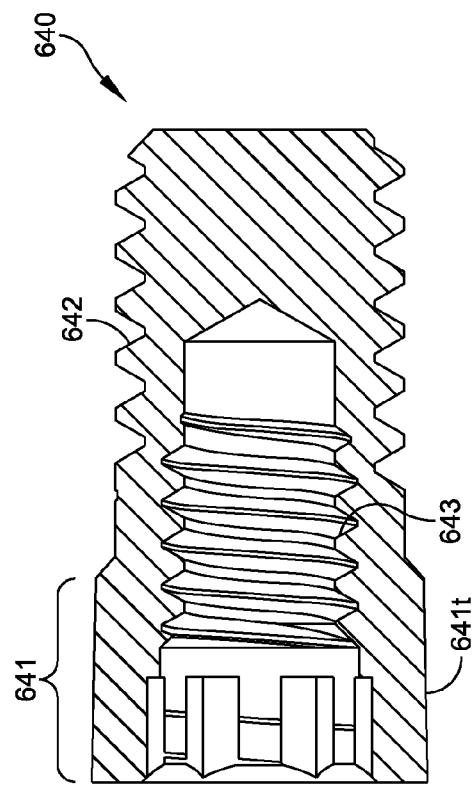
FIG. 15 is a cross sectional view of the cover screw of FIG. 6.
Figure 16:
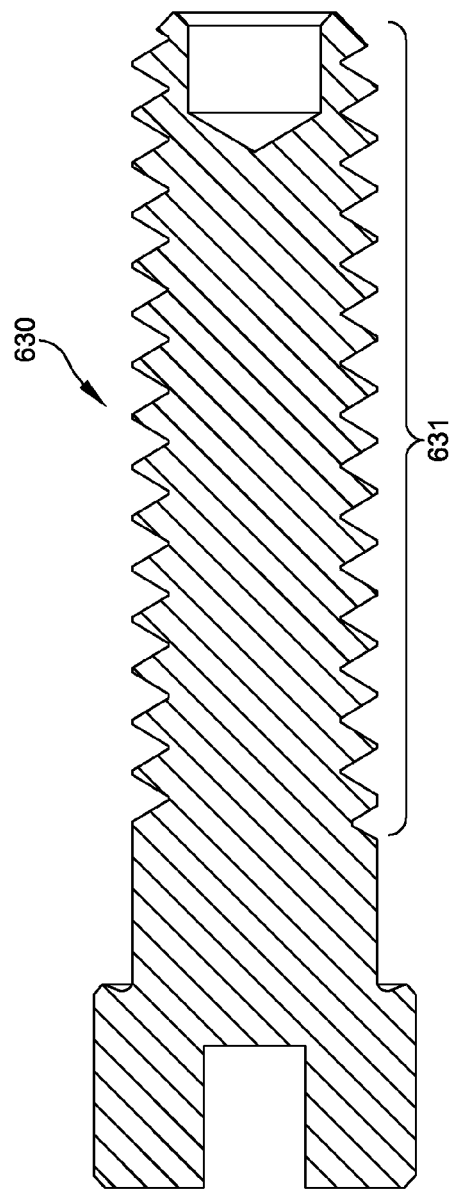
FIG. 16 is a cross sectional view of the draw screw of FIG. 6.

According to the embodiment in FIGS. 12 and 15, the expandable implant body 610 and the cover screw 630 together provide a Morse taper. The Morse taper provides a secondary seal that prevents infiltration of material from the bottom portion 621 of the expandable implant body 610 into the top portion 632, and vice versa. This prevents infiltration of material from the bottom of the implant into the abutment 660 and/or dental prosthesis (not shown) attached to the abutment. Various Morse tapers having taper angle ranging from 1° 25' 43" (Morse taper No. 1) to 1° 30' 26" (Morse taper No. 5) may be used. This range includes the Morse taper numbers 0 to 7.

In some embodiments, the cover screw 640 has a male first thread 642 receivable in the second top portion 633 of the body 610 and a female second thread 643 at a top end of the cover screw for securing the abutment 660 to the dental implant body 610. The step of fastening the abutment 660 includes passing a fastener 680 (FIG. 6) through an opening 668 in the abutment 660 and driving the fastener 680 into a threaded bore 643 in the sealing screw 640.

In some embodiments the body 610 has a taper 635 on an outer surface thereof, at or near the top end 625 of body. In the example, the top portion 637 of the implant body 610 has a head 636 adapted to be engaged by a tool for rotating the implant body, with the external tapered surface 635 positioned below the head. The head 636 may be hexagonal (FIGS. 10, 11) for rotating the body while tapping the bore 740 of the jaw bone. (In alternative embodiments, the head 636 may have another configuration, such as square, octagonal, or the like). The taper 635 is located adjacent the hexagonal head 636. The assembly 600 further comprises an abutment 660 having an internal surface 661 at a bottom end 665 of the abutment. The internal surface 661 has a taper sized and shaped to form a third seal with the outer surface 635 of the body 610. In some embodiments, the taper 635 of the body and the taper 661 in the abutment form a Morse taper. Various Morse tapers having taper angle ranging from 1° 25' 43" (Morse taper No. 1) to 1° 30' 26" (Morse taper No. 5) may be used. This range includes the Morse taper numbers 0 to 7. The Morse taper number of the seal between the tapered surface 635 of body 610 and the tapered surface 661 of the abutment may be the same as, or different from, that of the seal between the tapered surface 641 of the cover screw 640 and the tapered surface 632t of the body 610.

The bottom end of the abutment 660 has a cavity shaped to receive the hexagonal (or octagonal or square) head of the implant body 610, and the tapered surface 632. The Morse taper seal 632t, 661 between the body 610 and the abutment 660 prevents infiltration of fluid or material into the space between the abutment 660 and the implant body 610.

In the example described above, both the second seal (between the surface 632t of body 610 and the surface 641t of cover screw 640) and the third seal (between the surface 635 of body 610 and the surface 661 of abutment 660) are provided in an assembly 600 having an expandable implant body 610. In some alternative embodiments, the second seal is provided in an assembly 600 having an expandable implant body 610, without the third seal. In other alternative embodiments, the third seal is provided in an assembly 600 having an expandable implant body 610, without the second seal.

Although the example includes the second and third seals on an expandable implant body 610 having smaller threads 622a-622n in its bottom portion 621 than the threads 629 of the middle portion 628, other embodiments are contemplated. For example, the second seal, third seal, or both second and third seals may be used in an implant assembly where both the major and minor diameters of the thread are substantially constant across the middle and bottom portions of the body. Such an implant may be installed by first performing a separate tapping step, for example. In another example, the second seal, third seal, or both second and third seals may be used in an implant assembly where both the major and minor diameters of the thread are substantially constant across the middle portion of the body, but a smaller major diameter is used in the bottom portion of the body. Such an implant may also be installed by first performing a separate tapping step, for example.

Figure 17:
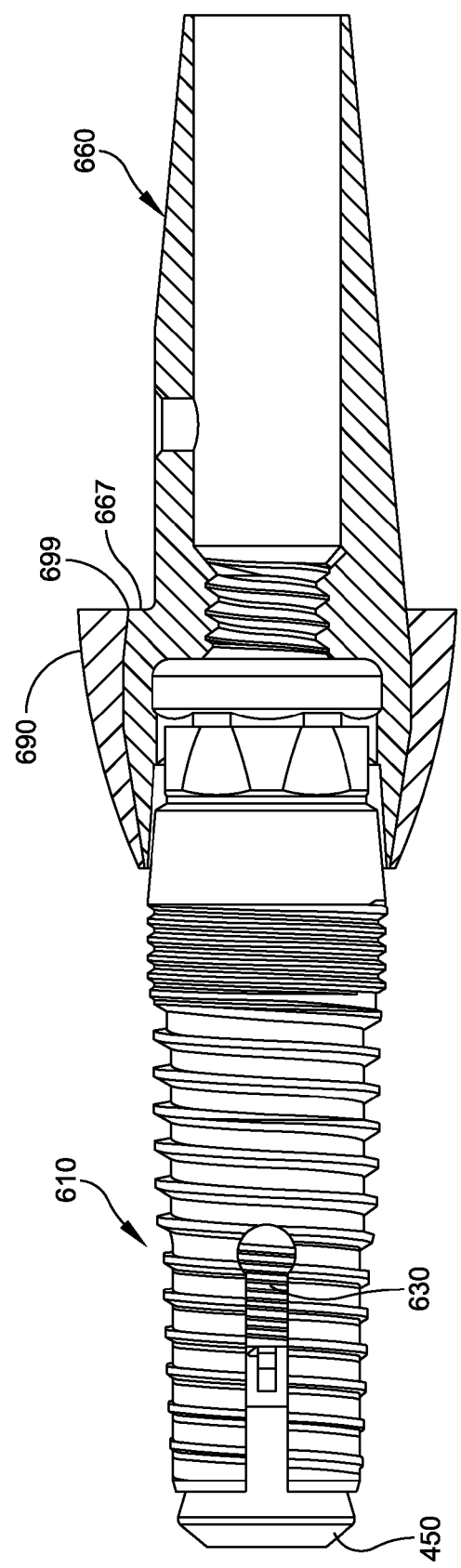
FIG. 17 is an assembly partial cross sectional view of the implant and abutment with attached cover.

Referring now to FIG. 17, the implant assembly 601 of FIGS. 6-12 is shown with an abutment 660 of FIGS. 13 and 14 attached. The abutment 660 has a top portion 664 and a bottom portion 663. The top portion 664 of the abutment 660 is adapted to secure a prosthetic component, The bottom portion 663 is configured to be attached to a top portion 637 of the body. In the example, the top portion 637 of the implant body 610 includes the first top portion 636 and the second top portion 635. The abutment 660 is formed of a first material, which may be a metal, such as ceramic, gold, titanium or a high noble metal alloy. The first material has a first color. A separate cover or ring 690 is provided. The cover 690 is configured to fit over and cover the bottom portion 663 of the abutment 660 without covering the top portion 664 of the abutment 660. The cover 690 is formed of a second material that is softer than the first material and has a different color from the first material. The cover 690 is joined to the abutment 660 by adhesive 699 (FIG. 17), a threaded joint (e.g., 692$t$ in FIG. 18D), or locking (e.g., key 664$k$ in FIG. 18E).

As best seen in FIG. 17, the bottom portion 663 of the abutment 660 is tapered, and the top portion 664 of the abutment is narrower than the bottom portion 663. The abutment 660 has a middle portion 663$m$ between the bottom 663 and top portion 664 of the abutment 660, and the cover 690 covers the bottom portion 663 and middle portion 663$m$. In some embodiments, (e.g., FIG. 17), the abutment 660 has a margin 667 and the top end of the cover 690 extends to the margin. In some embodiments, the thickness of the cover 690 approaches zero at the very bottom of the cover.

FIG. 18A shows a partial cutaway view of the abutment 660 with the cover 690. As shown in FIGS. 17 and 18A, the cover 690 has a wall thickness that decreases towards a bottom end of the cover. FIG. 18B is a view of the abutment and cover of FIG. 18A, taken along section line 18B-18B. In some embodiments, the cover 690 is pre-fabricated in a rotationally symmetric configuration, such as a frustum, and then ground by the doctor to a natural tooth contour, such as shown in FIGS. 18C-18E.

FIG. 18C shows an abutment 660 joined to a cover 691 having a three sided shape. FIG. 18C also shows a key 664$k$ for locking the cover 691 in place. In some embodiments, the key 664$k$ is placed on the part made of the stronger (in tensile, compressive and/or shear strength) material, which is typically the abutment 660. A corresponding groove is made in the cover 691, to receive the key 664$k$. Although FIG. 18C shows one kind of locking configuration, a variety of interlocking shapes may be used. For example, the bottom portion 663 of the abutment may have a square, hexagonal or octagonal outer cross section, and the interior shape of the cover may have the corresponding female configuration. The key may have a variety of cross-sectional shapes, such as rectangle, dove-tail, triangle, or the like.

FIG. 18D shows an abutment joined to a cover 692 of an elliptical shape. FIG. 18D also shows that the abutment 660 and cover 692 have a threaded joint 692$t$.

FIG. 18E shows an abutment 660 joined to a cover 693 of a quadrilateral shape. Although the shape of cover 693 is approximately trapezoidal with rounded corners, other quadrilateral shapes, such as a rectangle may be used.

In various embodiments, the second material is selected to match a color of a tooth or prosthetic tooth adjacent to the location where the implant is to be located. For example, the cover 690 may be formed of zirconium, ceramic or a dental composite resin. The material may be selected to have any "standard" color, such as a color selected from the Vita Shade Guide. The cover color may be selected to approximately match a color of the prosthetic component (e.g., 720, FIG. 19) to be attached to the abutment.

In some embodiments, the cover 690 and bottom portion 663 of the abutment 660 are adapted to be positioned below a gumline 730 (FIG. 19) of the patient. In a system where a bare metal abutment (without the cover 690) has its bottom portion positioned below the gumline 730, if the gums are less than 100% opaque, the effect may be to cause the gums in front of the abutment to appear gray. By locating the cover behind the gums, the gray appearance is avoided. Further, if the gums recede over time, the second material of the cover 690 is exposed, instead of the metal material of the abutment 660.

By separating the cosmetic component (cover 690) from the infrastructure component (abutment 660), the dentist is enabled to better customize the abutment/cover combination 660, 690. The dentist can purchase each part (abutment 660 and cover 690 preform) pre-fabricated, and then grind and/or polish the cover to any desired shape to fit the patient and emulate the shape of the tooth that is being replaced. Thus, the standardized, pre-fabricated cover 690 can be ground and/or polished to the contour of a natural tooth in that position. In some embodiments, the cover 690 is made entirely of the same second material, so that no matter how much material is removed by the doctor, the color of the cover 690 retains the same.

Figure 19:
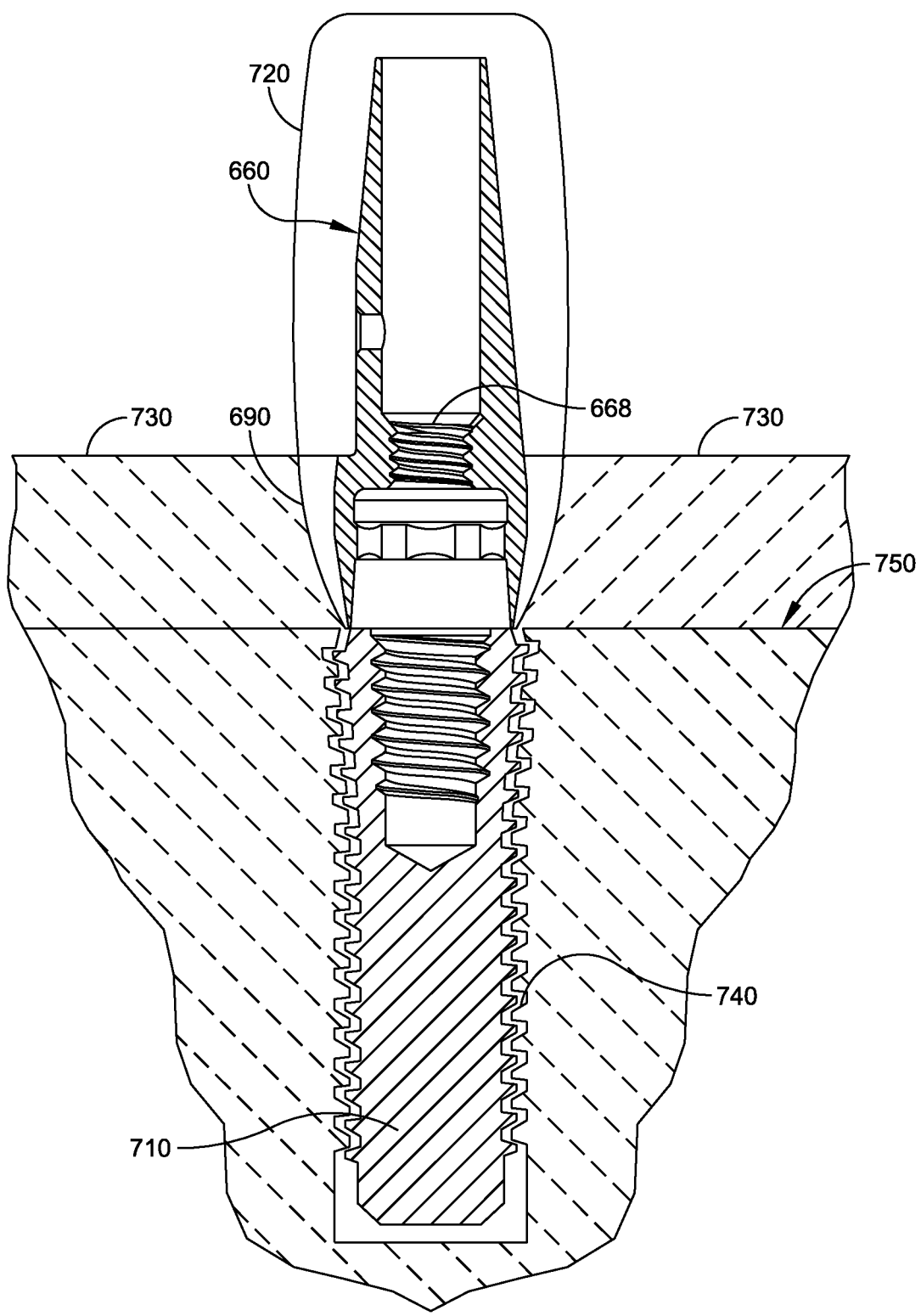
FIG. 19 is a cross sectional view of an assembly including another implant, the abutment, the cover, and prosthetic tooth installed in the bore of the patent's jaw.

Although FIG. 17 shows the abutment 660 and cover 690 used in combination with the dental implant of FIGS. 6-12, the combination of abutment 660 and cover 690 (or 691, 692, or 693) may be used in combination with other types of implants, including but not limited to expandable and non-expandable, screw type implants, implants with constant thread size or the "disappearing" treads 622$a$-622$n$ of FIG. 10, implants with or without a taper seal between the implant body and cover screw, and implants with or without a taper seal between the implant body and the abutment. For example, FIG. 19 shows a combination of a non-expandable screw type dental implant 710 having the abutment 660, and cover 690 attached, with the prosthetic device 720 attached to the abutment.

A method of using the abutment and cover combination comprises providing an abutment 660 having a top portion 664 and a bottom portion 663, the top portion of the abutment adapted to secure a prosthetic component 720 (FIG. 19), the abutment 660 formed of a first material. The bottom portion 663 of the abutment 660 is covered with a cover 690, without covering the top portion 664 of the abutment. The cover 690 is formed from a second material having a different color from the first material. The bottom portion of the abutment is secured to an implant body implanted within a bore 740 in a jaw bone of a patient. The cover 690 may be positioned below a gumline 730 of patient, with a top end of the cover 690 positioned approximately at the gumline 730.

Although the subject matter has been described in terms of exemplary embodiments, it is not limited thereto. Rather, the appended claims should be construed broadly, to include other variants and embodiments, which may be made by those skilled in the art.

What is claimed is:

1. A dental implant assembly, comprising:
a tubular body adapted for securement within a bore in a jaw bone of a patient, the body having an expandable bottom portion, the body having a first top portion with an internal taper on an inner surface thereof and a second top portion with an internal thread, the first top portion further having an external taper on an outer surface thereof opposite the internal taper, the external taper of the first top portion of the body and the internal taper on the inner surface of the body being coaxial with one another and overlapping one another;
a cover screw receivable in the top end of the body, the cover screw having a tapered head capable of forming a first taper seal with the internal taper of the first top portion for sealing an interior of the body; and
an abutment having an internal surface at a bottom end of the abutment with a taper sized and shaped to form a second taper seal with the outer surface of the first top portion,
the first taper seal between the cover screw tapered head and the internal taper of the first top portion and the second taper seal between the external taper of the first top portion and the internal surface of the abutment being located on opposite sides of the first top portion.

2. The dental implant assembly of claim 1, further comprising an expander, at least partially extending into the bottom end of the tubular body, for causing the bottom portion of the body to expand, the expander configured to be advanced from a first position in which the bottom portion of the body is not expanded and a second position in which the expander forces the bottom portion of the body to expand in diameter.

3. The dental implant assembly of claim 2, wherein the expander has a top end that extends into the body, the expander having an internal thread, the implant further comprising:
a rotatable draw screw within the interior of the body the body, the draw screw engaging the expander, so that rotation of the draw screw causes the expander to advance towards the top end of the body.

4. The dental implant assembly of claim 2, wherein the second taper seal is a Morse taper seal, and further comprising a draw screw within the body for advancing the expander, the cover screw having a first thread receivable in the second top portion of the body and a second thread at a top end of the cover screw for securing an abutment to the dental implant.

5. The dental implant assembly of claim 1, wherein the elongated tubular body has an outer thread on an outer surface thereof, the outer thread having a thread depth that gradually increases from a first major diameter near a bottom end of the body to a second major diameter near a top end of the bottom portion, the top end of the bottom portion located between the bottom end of the body and the top end of the body.

6. The dental implant assembly of claim 1, wherein a tightening of one of the first taper seal and the second taper seal increases structural support to the other one of the first taper seal and the second taper seal.

7. The dental implant assembly of claim 1, further comprising a cover configured to fit over and cover a bottom portion of the abutment without covering the top portion of the abutment, the abutment formed of a first material, the cover formed of a second material different from the first material.

8. The dental implant assembly of claim 7, wherein the second material is softer than the first material and has a different color from the first material.

9. The dental implant assembly of claim 7, wherein the body has an external tapered surface and the abutment has an internal tapered surface adapted to form a Morse taper seal with the external tapered surface.

10. The dental implant assembly of claim 9, wherein the body is adapted to be secured in the bone with the external tapered surface of the body extending above the bone.

11. The dental implant assembly of claim 9, wherein the body has an external hexagonal section at the top end, adjacent the external tapered surface.

12. The dental implant assembly of claim 1, wherein the abutment is configured to be above the bone when attached to the tubular body.

13. The dental implant assembly of claim 1, wherein the tubular body has an external hexagonal section above the external tapered surface.

14. The dental implant assembly of claim 1, further comprising the abutment having a top portion adapted to secure a prosthetic component, the bottom end of the abutment configured to be positioned below a gumline of the patient, with the bottom end shaped to attach to and fit over the tubular body.

15. The dental implant assembly of claim 14, wherein the top end of the tubular body has a head configured to be engaged by a tool for rotating the tubular body, with the external tapered surface positioned below the head.

16. The dental implant assembly of claim 14, wherein the bottom end of the abutment has an external taper and the abutment provides a margin between the bottom end and the top portion.

* * * * *